United States Patent [19]

Hrebeniuk

[11] Patent Number: Plant 6,496

[45] Date of Patent: Dec. 27, 1988

[54] POINSETTIA PLANT NAMED HL1—HOT PINK

[76] Inventor: Alexander Hrebeniuk, R.D. #1, Box 118, Sugar Run, Pa. 18846

[21] Appl. No.: 44,461

[22] Filed: May 1, 1987

[51] Int. Cl.[4] ..... A01H 5/00

[52] U.S. Cl. ..... Plt./86

[58] Field of Search ..... Plt./86

*Primary Examiner*—Robert E. Bagwill

*Attorney, Agent, or Firm*—Schwartz, Jeffery, Schwaab, Mack, Blumenthal & Evans

[57] ABSTRACT

A new Poinsettia cultivar named HL1—Hot Pink, characterized by its hot pink flower color, double flowers, excellent breaking, early and long blooming, tolerance to low growing temperatures, compact habit, and by its excellent keeping and shipping qualities.

1 Drawing Sheet

The present invention relates to a new and distinct cultivar of Poinsettia plant currently referred to by the cultivar name HL1—Hot Pink, and botanically known as *Euphorbia pulcherrima.*

The new cultivar is an induced mutation of applicant's cultivar referred to during development as HL1—Red. The parent cultivar is disclosed in U.S. Plant Pat. No. 4,434, and is being commercialized under the cultivar designation Noel.

The new cultivar HL1—Hot Pink resulted from the subjecting of plants of the parent cultivar to radiation at a level of 2000 rads by applicant in Sugar Run, Pa. The irradiated plants subsequently flowered, and HL1—Hot Pink was selected from the flowering group in November, 1985 at the indicated location.

The first act of asexual reproduction of HL1—Hot Pink was accomplished when vegetative cuttings were taken by applicant from the initial selection in January 1986 in a controlled environment in Sugar Run, Pa. Horticultural examination of selected units initiated in August 1986 has demonstrated that the combination of characteristics as herein disclosed for HL1—Hot Pink are firmly fixed and are retained through successive generations of asexual reproduction.

HL1—Hot Pink has not been observed under all possible environmental conditions. The phenotype may vary significantly with variations in environment such as temperature, light intensity, and day length. The following observations, measurements and comparisons describe plants grown in Sugar Run, Pa. under greenhouse conditions which approximate those generally used in commercial practice.

The following traits have been repeatedly observed and are determined to be basic characteristics of HL1—Hot Pink which in combination distinguish this Poinsettia as a new and distinct cultivar:

1. The ability to produce 10 branches from a single pinched plant without chemical treatment.
2. Starts blooming well before Christmas, as early as the second week in November, and stays in bloom for three months, without loss of foliage or flowers.
3. Can be initially grown at 58 degrees F., and the temperature can be lowered to 50 degrees F. when half bloomed.
4. Double flowers which are resistant to fade.
5. Can be watered without "dark spotting".
6. Hardy foliage which is resistant to drooping.

7. Self-branching, with many branches being produced.
8. Fast rooting cuttings.
9. Pointed leaves.
10. Resists bruising, making HL1—Hot Pink excellent for shipping.
11. Compact plant and has decreased tendency of the butts to separate.
12. The foliage and flowers retain their color for a relatively long period of time without fading, whether or not the plant is exposed to sun.
13. The new cultivar appears to be very resistant to root rot.

HL1—Hot Pink is generally similar in all characteristics except color to its parent cultivar Noel and to another mutation of Noel, HL1—Pink and White, disclosed in my copending application. The bract color of Noel is a much more vivid red. The bract color of HL1—Pink and White is a variegated pink and cream, with the pink being much lighter than the intense pink of HL1—Hot Pink.

The new cultivar can also be compared to the commercial cultivar Annette Hegg Pink, disclosed in U.S. Plant Pat. No. 3,099. The bract color is generally similar although HL1—Hot Pink is more pink as opposed to red, and the respective bract and leave shapes are distinguishably different. In addition, HL1—Hot Pink has better keeping and shipping qualities, and has a more compact habit.

The accompanying photographic drawing shows typical bract and foliage shapes and colors of HL1—Hot Pink, which appears on the left, and Annette Hegg Pink, which appears on the right.

In the following description color references are made to The Royal Horticultural Society Colour Chart. The color values were determined at approximately 2:15 p.m. on Jan. 5, 1987 under florescent light at Parrish, Fla.

Classification:

*Botanical.—Euphorbia pulcherrima.*

*Commercial.—Poinsettia.*

Parentage: Sport of Noel.

Plant description:

(A) *Form.*—Double.

(B) *Growth habit.*—Upright, medium height and self-branching.

(C) *Rooting.*—Very fast, roots develop within two weeks and are rot resistant.

(D) *Blooming season.*—Nine week variety, starting mostly in the second week of November.

(E) *Blooming habit.*—Large bracts in double rows.

Foliage:

(A) *Size.*—Up to 20 cm long and 9 cm wide.

(B) *Quantity.*—10 to 20 leaves or more.

(C) *Color.*—New foliage: Upper side, 147B; Under side, 147C. Old foliage: Upper side, 147A; Under side 147B.

(D) *Shape.*—Generally ovate, venation midrib to margin; tips apiculate.

(E) *Texture.*—Upper side, flat. Under side, smooth.

(F) *Edge of margin.*—Repand.

(G) *Disease resistance.*—Resistance observed to root rot.

Flowers:

(A) *Borne.*—Compound corymb.

(B) *Quantity.*—Excellent.

(C) *Continuity.*—Flowers continuously for up to three months.

Bracts:

(A) *Size.*—Up to 20 cm long and 9 cm wide.

(B) *Quantity.*—From 18–20 per stem.

(C) *Shape.*—Ovate with a repand margin.

(D) *Color.*—51A

Reproductive organs: Typical Poinsettia, insignificant.

I claim:

1. A new and distinct cultivar of Poinsettia named HL1—Hot Pink, as illustrated and described.

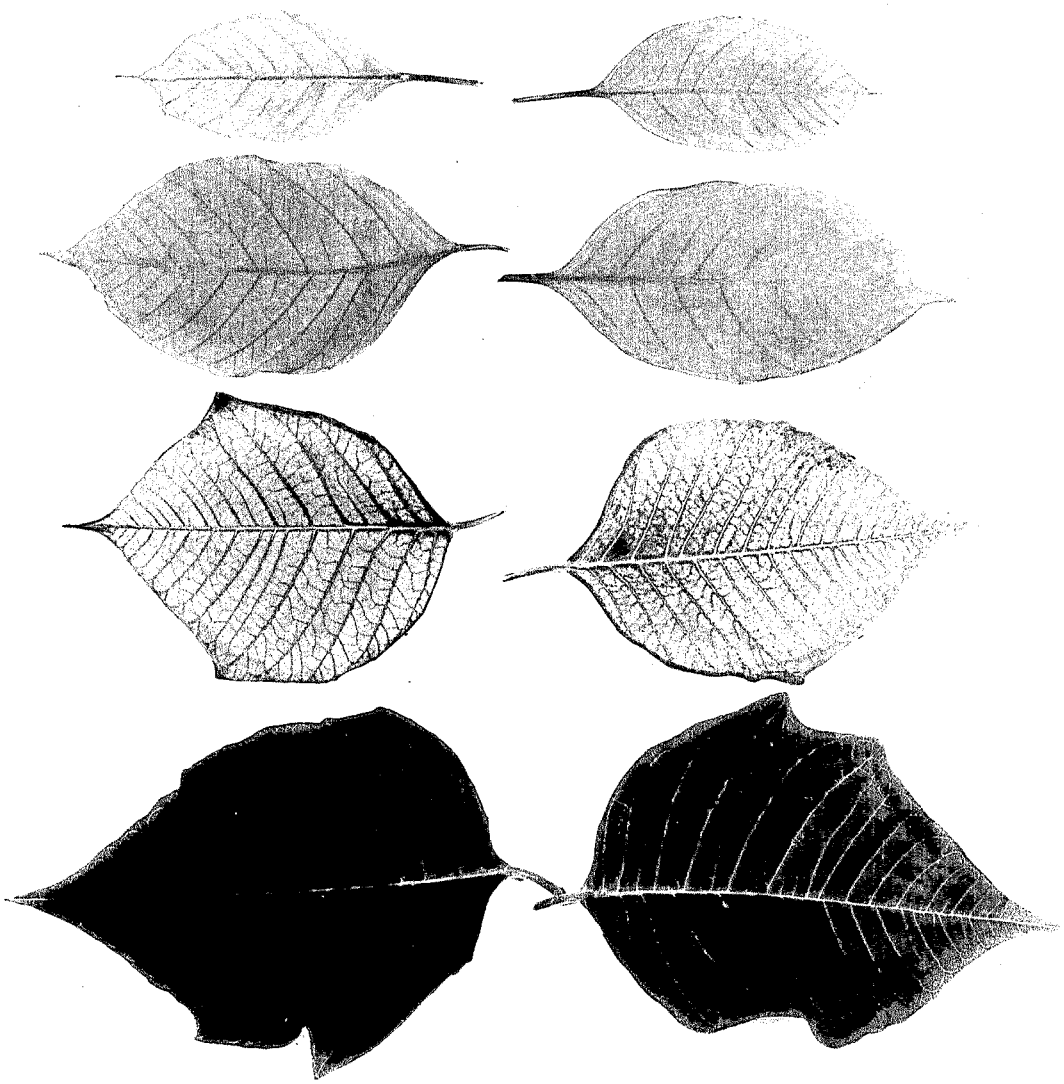

* * * * *